(12) United States Patent
Wright

(10) Patent No.: US 8,556,965 B2
(45) Date of Patent: Oct. 15, 2013

(54) SEMI-RIGID ANNULOPLASTY RING AND BAND

(75) Inventor: John T. M. Wright, Denver, CO (US)

(73) Assignee: Medtronic, Inc., Minneapolis, MN (US)

( * ) Notice: Subject to any disclaimer, the term of this patent is extended or adjusted under 35 U.S.C. 154(b) by 742 days.

(21) Appl. No.: 12/643,073

(22) Filed: Dec. 21, 2009

(65) Prior Publication Data

US 2010/0168845 A1 Jul. 1, 2010

Related U.S. Application Data

(60) Provisional application No. 61/142,073, filed on Dec. 31, 2008.

(51) Int. Cl.
*A61F 2/06* (2013.01)

(52) U.S. Cl.
USPC .......................................... 623/2.36; 623/2.37

(58) Field of Classification Search
USPC ................................................ 623/2.36–2.41
See application file for complete search history.

(56) References Cited

U.S. PATENT DOCUMENTS

| | | | |
|---|---|---|---|
| 5,201,880 A | 4/1993 | Wright | |
| 5,306,296 A | 4/1994 | Wright | |
| 5,674,279 A | 10/1997 | Wright | |
| 6,143,024 A | 11/2000 | Campbell | |
| 6,187,040 B1 * | 2/2001 | Wright | 623/2.36 |
| 6,955,689 B2 | 10/2005 | Ryan | |
| 2007/0067028 A1 | 3/2007 | Wright | |
| 2007/0179603 A1 | 8/2007 | Wright | |
| 2008/0208331 A1 | 8/2008 | McCarthy | |

OTHER PUBLICATIONS

International Search Report from PCT/US2009/069040, dated Aug. 17, 2010.

* cited by examiner

*Primary Examiner* — David Isabella
*Assistant Examiner* — Suba Ganesan

(57) ABSTRACT

An annuloplasty ring comprising an elongate tube of suturable material formed into a ring. A stiffener configured to prevent axial compression and radial deformation of the ring is received in the tube in a first circumferential segment of the ring. An axial support configured to prevent axial compression of the ring and to permit radial deformation of the ring is received in the tube in a second circumferential segment of the ring. The first circumferential segment of the ring may correspond to a posterior portion of a mitral valve annulus with the first circumferential portion configured to extend between the right and the left fibrous trigones of the mitral valve annulus upon installation. The second circumferential segment of the ring may correspond to an anterior portion of a mitral valve annulus and the second circumferential segment is configured to extend between the right and left fibrous trigones of the mitral valve annulus upon installation.

14 Claims, 12 Drawing Sheets

SEMI-RIGID ANNULOPLASTY RING AND BAND

RELATED APPLICATIONS

This application claims priority from U.S. Provisional Patent Application Ser. No. 61/238,944, filed Dec. 31, 2008, entitled "Semi-Rigid Annuloplasty Ring and Band," which is hereby incorporated by reference.

TECHNICAL FIELD

Annuloplasty rings for mitral or tricuspid heart valve repair, and more particularly a semi-rigid annuloplasty ring and band.

BACKGROUND

It is well known in the field of heart valve repair to use implantable annuloplasty rings for surgical correction of certain mitral or tricuspid heart valve disorders. Clinical experience has shown that the repair of heart valves, where this technique is possible, produces significantly better long term results than do valve replacements.

Wright, U.S. Pat. No. 5,674,279, the contents of which are expressly incorporated by reference herein, describes in detail various effects of valvular dysfunction, known corrective procedures and various prosthesis that have been used in conjunction with mitral or tricuspid valve repair. Wright is also directed to an annuloplasty ring structure that has experienced considerable success in both mitral and tricuspid valve repair.

Known annuloplasty rings are either completely flexible or have an internal frame in at least a portion of the annuloplasty ring to impart some structural rigidity. Those annuloplasty rings with a rigid internal frame (i.e., a frame is rigid both along a circumferential axis of the frame and radially relative to the circumferential axis) can interfere with normal movement of the mitral valve annulus during diastole and systole. More particularly, during diastole the mitral valve annulus assumes a substantially planar configuration. During systole the anterior leaflet of the mitral valve bows into the left atrium due to aortic pressure, forming the mitral valve annulus into a partially flattened saddle shape. A rigid annuloplasty ring can interfere with the anterior segment of the mitral valve annulus assuming this bowed configuration during systole, leading to a condition known as systolic anterior motion or SAM. Thus, this is one limitation of the Carpentier-Edwards D-Shaped "Classic" semi-closed ring discussed in the Wright '279 patent, and the Carpentier-Edwards "Physio" ring.

Other rings are flexible, such as the Cosgrove-Edwards band, which is a fully flexible C-shaped ring and the Medtronic Duran ring, which is fully flexible and circular. Both of these rings are also discussed in the Wright '279 patent. Because flexible annuloplasty rings can be hard for surgeons to manipulate and implant due to their flexible nature, flexible rings and bands typically require a holder for implantation by a surgeon. Moreover, flexible rings are subject to axial compression or bunching when implantation sutures are tightened and tied during implantation.

The present invention is directed toward overcoming one or more of the problems discussed above.

SUMMARY OF THE EMBODIMENTS

A first aspect of the embodiments is an annuloplasty ring comprising an elongate tube of suturable material formed into a ring. A stiffener configured to prevent axial compression and to resist radial deformation of the ring is received in the formed tube in a first circumferential segment of the ring. As used herein, "axial compression" means along a circumferential axis of the ring and "radial deformation" means deformation radially (or transverse) of the circumferential axis. Thus, "radial deformation" includes deformation in the same or opposite direction of blood flow with the annuloplasty ring implanted on a heart valve annulus. As used herein, "resist radial deformation" means providing sufficient radial rigidity to prevent radial deformation of greater than 0.3 inches with a load of 25-75 grams (depending on the ring or band size, which for the embodiments described herein generally vary between about 40-24 mm across the trigones) applied across a major diameter, but to permit a substantially normal range of axial movement of a posterior portion of a mitral valve annulus with the annuloplasty ring installed on a mitral valve annulus and depicted in FIG. 7. In other words, with the first circumferential segment of the ring attached to the posterior portion of the mitral valve annulus between the right and left trigones. The qualifier "substantially" means the qualified function or property occurs without material interference diminishing its intended effectiveness. An axial support configured to prevent axial compression of the ring and to permit substantially free radial deformation of the ring is received in the tube in a second circumferential segment of the ring. As used herein, "substantially free radial deformation" means sufficient radial rigidity to prevent radial deformation of greater than 0.3 inches with a load of 25-75 grams (depending on the ring diameter) applied across the major diameter, but to permit a substantially normal range of axial movement of an anterior portion of a mitral valve annulus with an annuloplasty ring installed with the second circumferential segment of the ring attached to an anterior portion of a mitral valve annulus, as depicted in FIG. 7. In one embodiment a close-coiled spring formed into a ring corresponding to the ring of suturable material is received inside the tube. In this embodiment the stiffener comprises a metal wire axially received in a cavity defined by the circumferential portion of the close-coiled spring corresponding to the first circumferential segment. In this embodiment the axial support comprises a circumferential portion of the close-coiled spring corresponding to the second circumferential segment not having a metal wire axially received therein. The first circumferential segment of the ring may correspond to a posterior portion of a mitral valve annulus with the first circumferential portion configured to extend between the right and the left fibrous trigones of the mitral valve annulus upon implantation. The second circumferential segment of the ring may correspond to an anterior portion of a mitral valve annulus and the second circumferential segment is configured to extend between the right and left fibrous trigones of the mitral valve annulus upon implantation. The suturable material may be a braided heat settable material. The heat settable material may be polyethertetraphylate heat set into the desired cross-sectional configuration.

Another aspect is a method of making an annuloplasty ring. The method includes providing a length of a close-coiled spring. A pre-formed stiffener is inserted into a cavity formed by the spring coils and axial movement of the stiffener within the cavity is prevented. The close-coiled spring is formed into a ring by securing the ends of the length of close-coiled spring together. A ribbon of suturable material is provided and formed into a ring by securing its ends together. The close-coiled spring formed into a ring is placed into contact with the ring of suturable material and the ring of suturable material is formed into a ring surrounding the close-coiled spring. The method may further include securing the close-coiled spring to the tube to prevent circumferential movement of the close-coiled spring within the tube. The method may further include inserting the close-coiled spring within an elastomeric tube. An elastomeric core may be inserted into the cavity formed by the spring coils with the elastomeric core having a length sufficient such that, with the spring formed in the ring, the elastomeric core prevents axial movement of the stiffener within the cavity.

Yet another aspect is an annuloplasty ring band comprising an elongate tube of suturable material. A stiffener configured to prevent axial compression and to resist radial deformation of the ring is formed into a C-shape and sized and shaped to conform to a posterior portion of a mitral valve annulus extending between left and right trigones of the mitral valve annulus. The stiffener may comprise a close-coiled spring and a metal wire axially received in a lengthwise cavity of the close-coiled spring. A cap of a circular cross section with a chamfered edge may be provided at each end of the stiffener with the caps being configured to prevent the stiffener ends from protruding through the suturable material. The metal wire may be made of a bio-compatible metal having a diameter in a range of 0.015 and 0.050 inches. The bio-compatible metal may be a Carpenter MP35N alloy.

The semi-rigid annuloplasty ring in accordance with the present embodiments provides a circumferential segment for providing desired axial rigidity while resisting radial deformation and an axially rigid and radially flexible circumferential segment which is conformable to valve anatomy when such conformity is required. In the particular application of an annuloplasty ring for a mitral valve repair, an annuloplasty ring in accordance with the present embodiments provides a posterior portion which is axially rigid while resisting radial deformation attachable to the mitral valve annulus between the left and right fibrous trigones and an axially rigid but radially flexible anterior segment attachable to the anterior portion of the mitral valve. The flexible annular portion can accommodate bowing of the anterior annulus out of the normal plane of the annulus into the left atrium as a result of aortic pressure during systole of a normally beating heart. The axial stiffness of the anterior segment prevents bunching of the annuloplasty ring suturable material cover during implantation and subsequent implantation suture tying. The semi-rigid annuloplasty band provides many of the advantages of the semi-rigid annuloplasty ring and meets the needs of surgeons that prefer a band with no anterior segment to the ring having an axially rigid and radially flexible circumferential posterior segment.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
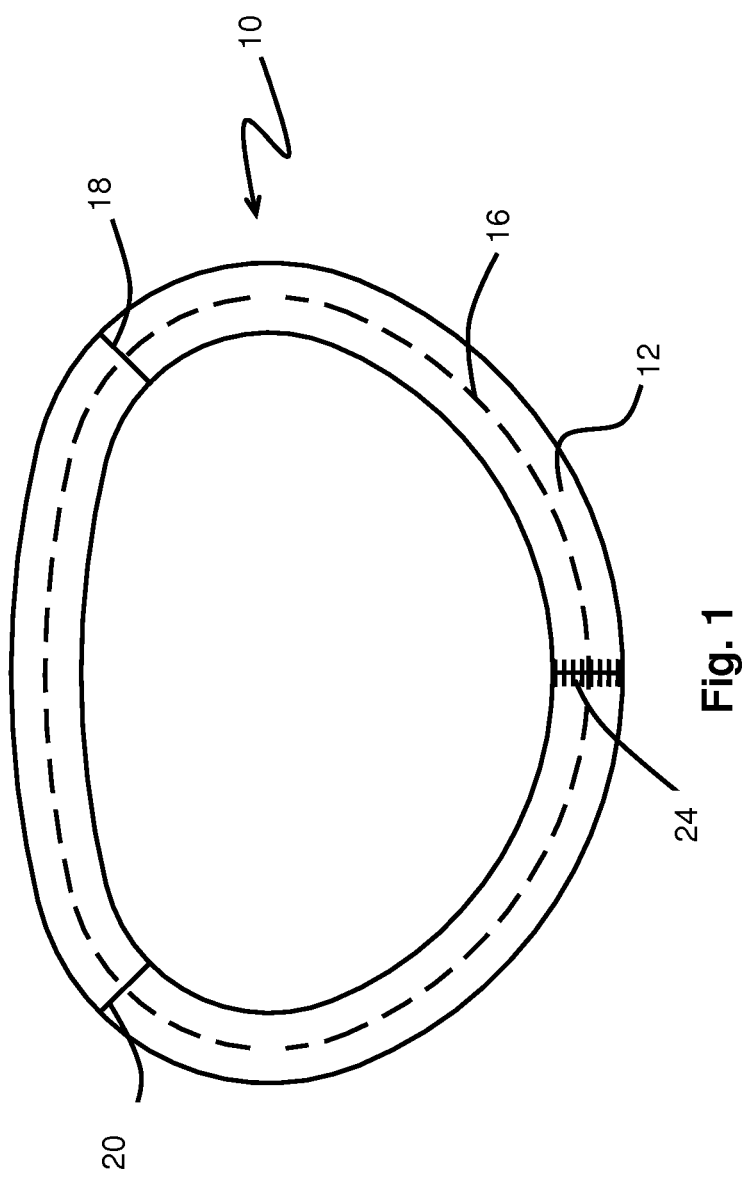
FIG. 1 is a plan view of a semi-rigid annuloplasty ring.

A semi-rigid annuloplasty ring 10 is shown in a plan view in FIG. 1. As seen in FIG. 1, the semi-rigid annuloplasty ring 10 comprises an elongate tube of suturable material 12 formed into a ring. In one specific embodiment described herein, the suturable material may be a biocompatible ribbon of heat settable material heat set into a tubular configuration as described in Wright, U.S. Pat. No. 5,674,279, the disclosure of which is hereby incorporated in its entirety herein. An example of a suitable heat settable material is Polyethertetraphylate (Polyester). Embodiments could also include other suitable woven or braided biocompatible materials such as Nylon or other biocompatible materials. The material must be suitable to readily receive a needle carrying a suture, a suture clip or other similar securing means and be capable of maintaining a position on an annulus of a heart valve without fraying once secured in place.

Various markers may be provided on the suturable material to aid a surgeon during installation of the semi-rigid annuloplasty ring 10 onto a valve annulus. For example, the embodiment illustrated in FIG. 1 is intended for installation on a mitral valve annulus. In this embodiment, the markers include a demarcation marker 16, a right trigone marker 18 and a left trigone marker 20. The demarcation marker 16 provides a visual indication to a surgeon of where sutures or suture clips can be placed without the needle or clip used for implanting interfering with an interior stiffener assembly or operation of the semi-rigid annuloplasty ring 10. The right trigone marker 18 and the left trigone marker 20 are positioned to correspond to the right fibrous trigone and the left fibrous trigone, respectively, of a mitral heart valve and aid the surgeon in correctly placing the semi-rigid annuloplasty ring 10 on the mitral valve annulus. In an embodiment configured for use with, for example a tricuspid annulus, other markers may be provided. In addition, in such an embodiment the semi-rigid annuloplasty ring 10 may have a more circular footprint than the substantially D-shaped footprint of the embodiment of a mitral valve annuloplasty ring 10 depicted in FIG. 1.

Figure 2:
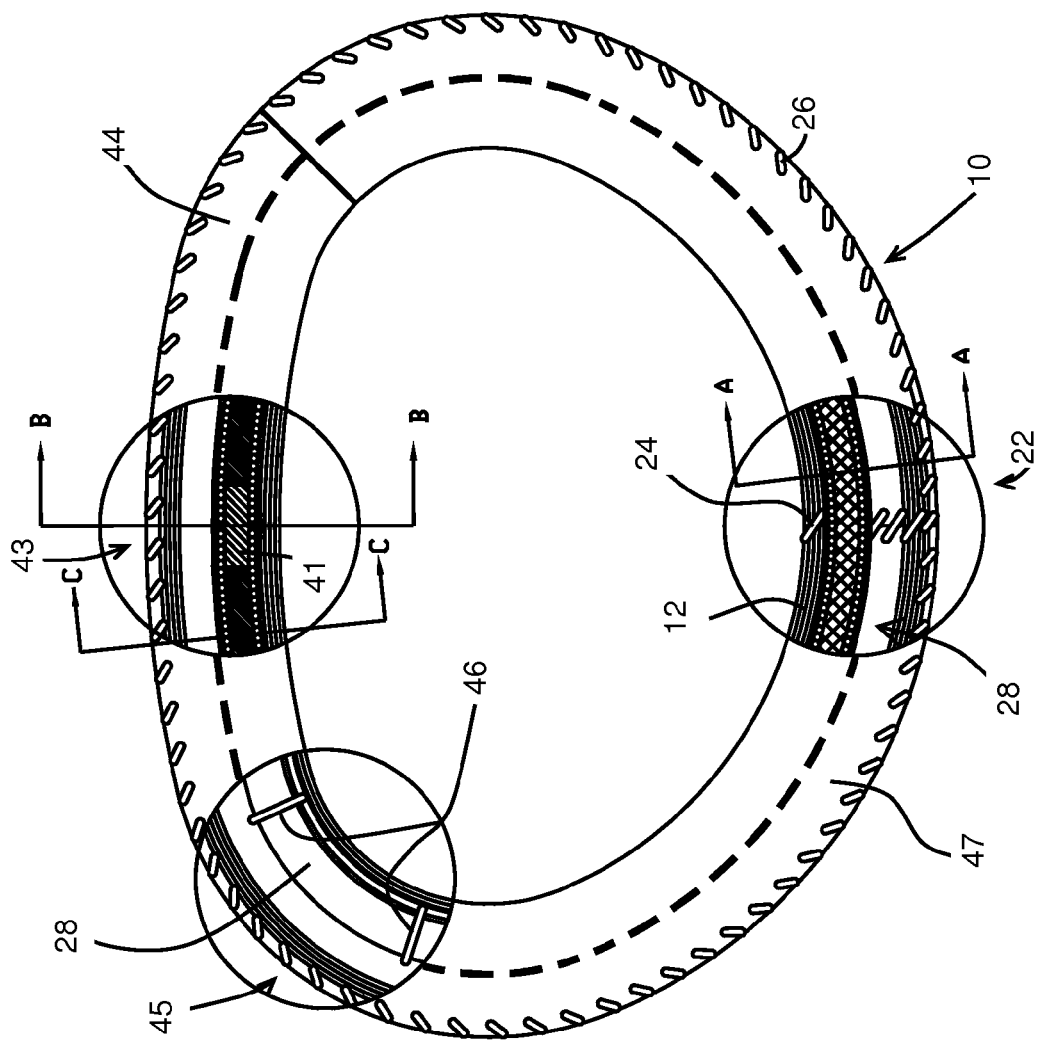
FIG. 2 is a plan view of the semi-rigid annuloplasty ring of FIG. 1 with portions cut away to reveal the internal construction.
Figure 3:
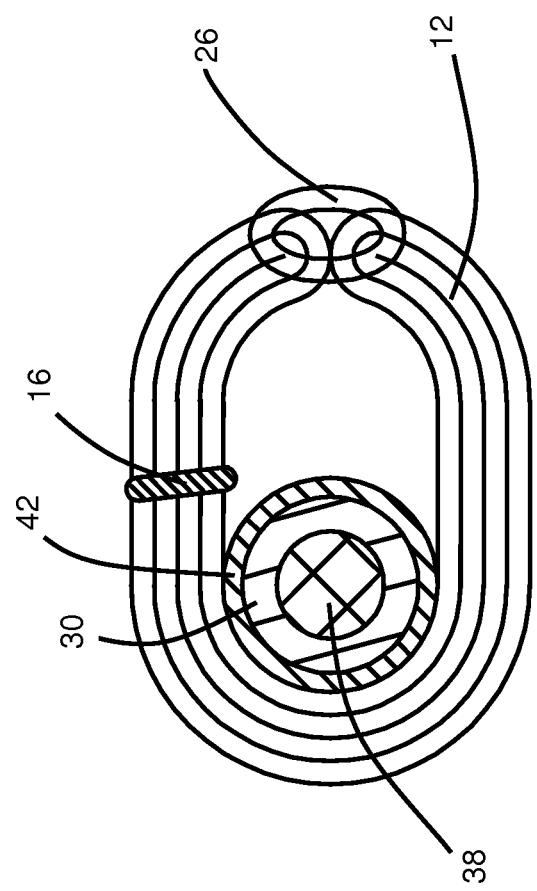
FIG. 3 is a cross-section taken along line A-A of FIG. 2.
Figure 4:
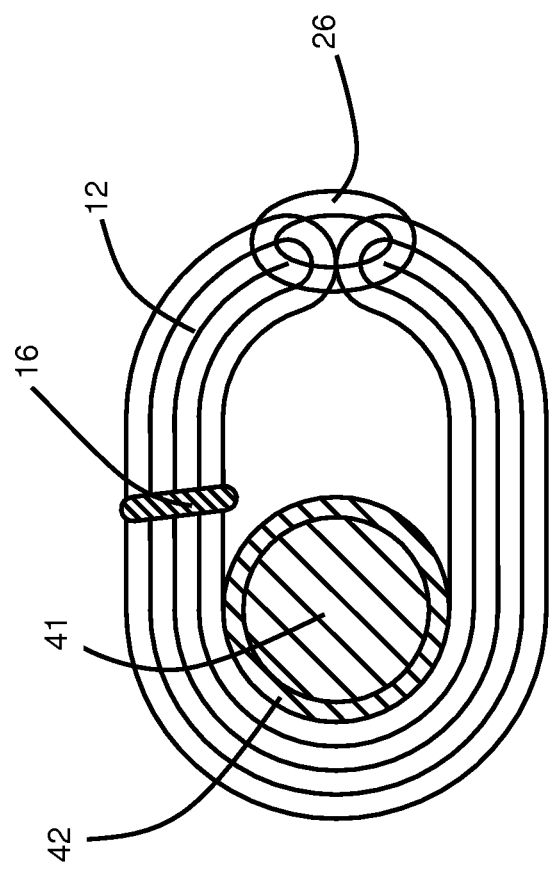
FIG. 4 is a cross-section taken along line B-B of FIG. 2.
Figure 5:
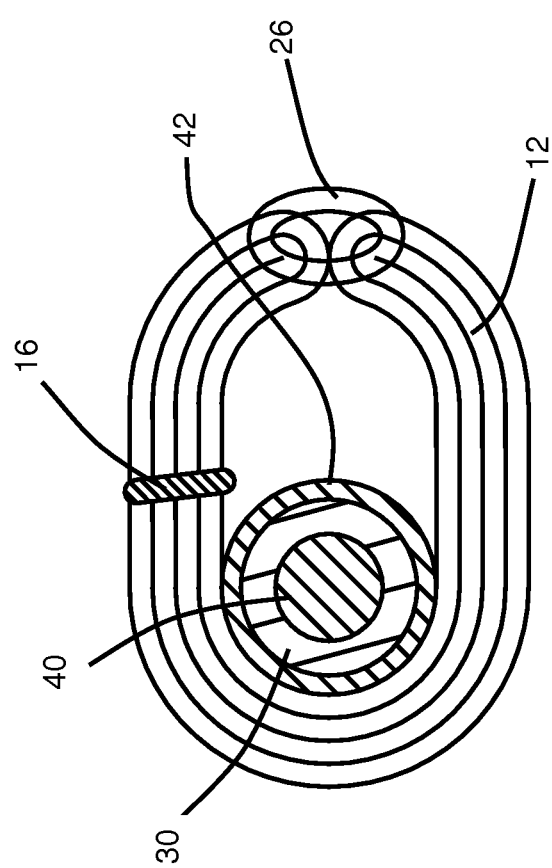
FIG. 5 is a cross-section taken along line C-C of FIG. 2.

FIG. 2 depicts the semi-rigid annuloplasty ring 10 of FIG. 1 with various cutaway portions to illustrate the internal structure of the semi-rigid annuloplasty ring 10. Referring to the bottom cutaway portion 22, the suturable material 12 is seen to comprise a number of layers as described in the Wright '279 patent referenced above. The suturable material 12 is formed into a ring by means of radial stitching forming a radial seam 24 and into a tube by means of circumferential stitching forming a circumferential seam 26.

Figure 6:
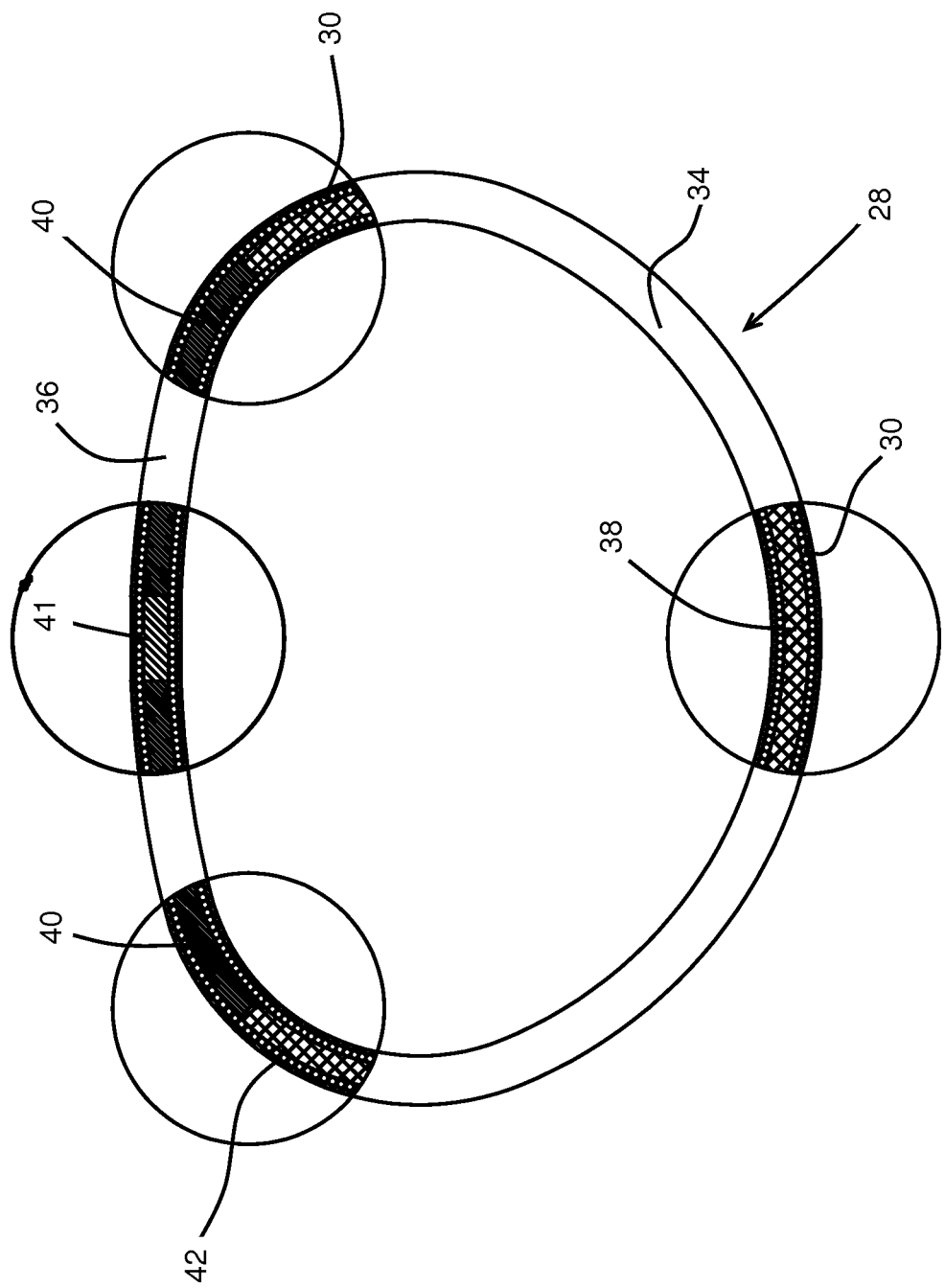
FIG. 6 is a plan view of a semi-rigid stiffener of the annuloplasty ring of FIG. 1 with the suturable cover removed and portions of the stiffener shown in lengthwise cross-section.

Within the semi-rigid annuloplasty ring 10 resides a stiffener assembly 28. The stiffener assembly 28 is best viewed in FIG. 6. The stiffener assembly 28 comprises a close-coiled spring 30 of a biocompatible metal such as a Carpentier MP35N alloy. The spring may preferably be wound using 0.009-0.012 inch diameter wire, although other wire diameters in the range of 0.005-0.020 inches are suitable. The spring has an inside diameter of approximately 0.029 inches and an outside diameter of approximately 0.055 inches. The helical coils of the spring define a spring cavity. The stiffener assembly 28 is generally divided into two circumferential segments, a first circumferential segment 34 and a second circumferential segment 36. The first circumferential segment 34 comprises a stiffener 38 which is configured to prevent axial compression and to resist radial deformation of the first circumferential segment. A stiffener wire 38 is axially received in the spring cavity of the first circumferential segment 34 of the stiffener assembly 28 to provide the resistance to axial and radial deformation. The stiffener wire 38 may be, for example, a biocompatible metal of the same composition as the spring to prevent galvanic corrosion. The stiffener wire should be of a diameter to resist radial deformation, as this phrase is defined above. By way of example, where the semi-rigid annuloplasty ring or band is to be used for a mitral valve and the stiffener assembly, a MP35N alloy, a diameter of 0.028 inches providing good results and a range of 0.015-0.050 inches (depending upon the desired stiffness and the ring or band size) generally being acceptable. For example, stiffeners formed from 0.028 inches diameter MP35N wire with a tensile strength of 240 ksi gave the following results (Table 1).

in place by an interference fit. In the illustrated embodiment, a silicone rubber tube 42 receives the close-coiled spring 30.

In an embodiment where the stiffener assembly 28 is to be used in a semi-rigid annuloplasty ring for mitral valve repair, the first circumferential segment 34 is configured to correspond in shape and size to a posterior portion of the mitral valve annulus with the first circumferential segment 34 extending between the right and left fibrous trigones on installation. The second circumferential segment 36 is configured to correspond to an anterior portion of a mitral valve annulus and the second circumferential segments 36 extends between the right and left fibrous trigones of a mitral annulus upon installation.

The tube of suturable material 12 may be formed in a manner discussed in the Wright '279 patent. With the suturable material formed into a ring having a V-cross section, the stiffener assembly 28 is placed therein with tack stitches 46 (see FIG. 2) spaced circumferentially around the circumference of the stiffener assembly. Thereafter the radial seam 26 is provided to close the tube. The demarcation marker 16 and the right and left trigone markers 18, 20 can then be added. In an embodiment where the suturable material is a heat settable material, a further step of heat setting the radial seam 26 of the semi-rigid annuloplasty ring 10 may be included.

Referring again to FIG. 2, the top cut away portion 43 shows the spring coupler 41 positioned in the middle of the anterior or second circumferential segment 44 of the semi-rigid annuloplasty ring, which corresponds to the second circumferential segment 36 of the stiffener assembly. The cut away portion 45 illustrates the tack stitches 46 securing the stiffener assembly 28 to the tube of suturable material 12. The posterior or first circumferential segment 47 of the semi-rigid annuloplasty ring 10 corresponds to the first circumferential segment 34 of the stiffener assembly 28.

Figure 7:
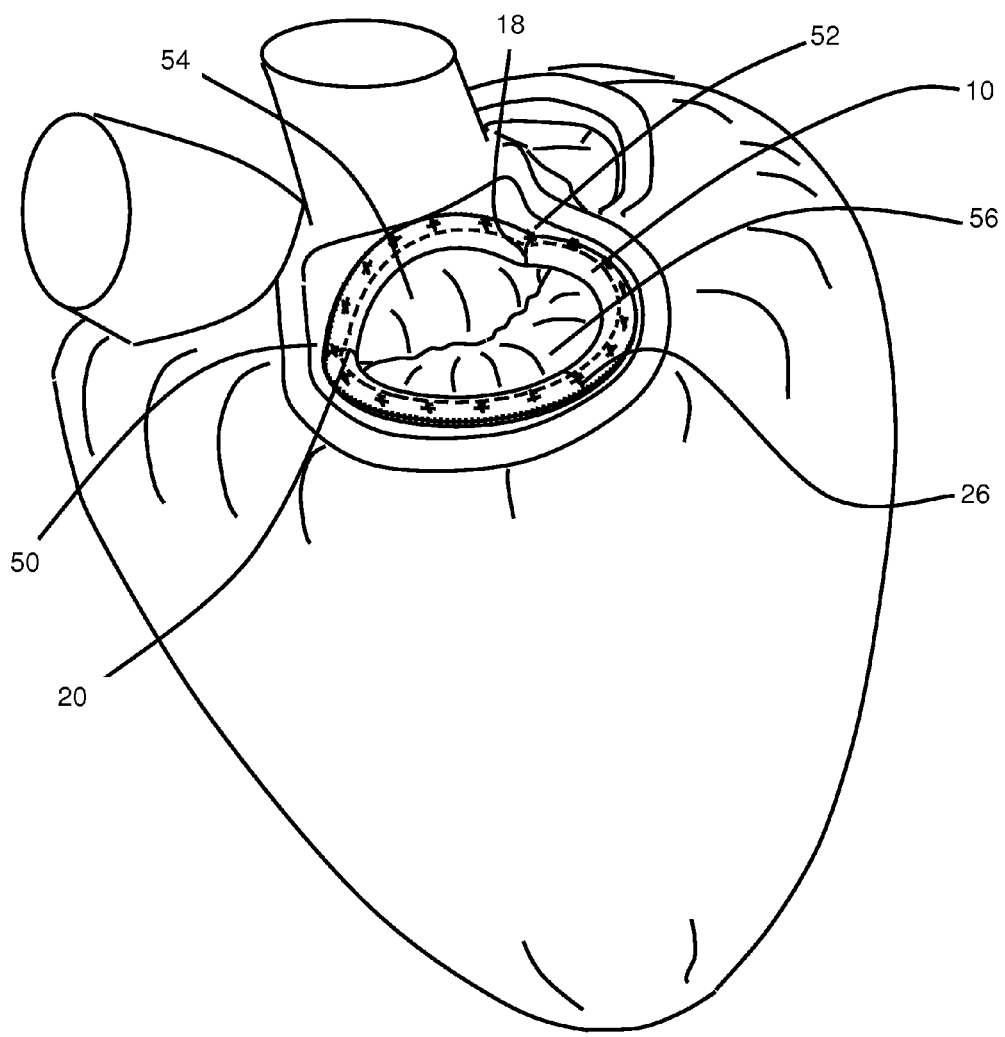
FIG. 7 is an isometric view of a semi-rigid annuloplasty ring of FIG. 1 sewn into the mitral annulus of a heart during ventricular systole.

FIG. 7 is an isometric view of the semi-rigid annuloplasty ring 10 of FIG. 1 attached to the mitral annulus of a heart (the left atrium is removed for clarity of illustration). The heart is

TABLE 1

Static Loads to produce stated deflections of stiffener, complete rings and complete bands

| | | | Load (Pounds) at Stated deflection | | Load increase of Complete Ring and Band compared to bare stiffener | |
|---|---|---|---|---|---|---|
| Ring and Band Size (across the trigones) | Radial Deflection inches | Wire Stiffener only | Complete Ring, Anterior Segment allowed to buckle | Complete Band | Complete Ring, Anterior Segment allowed to buckle | Complete Band |
| 24 mm | 0.150 | 0.72 | 1.14 | 0.75 | 158% | 104% |
| 40 mm | 0.500 | 0.71 | 1.48 | 0.74 | 208% | 104% |

In the second circumferential segment a silicone rubber core 40 is received in the spring cavity. The silicone rubber core 40 act primarily as stop to prevent circumferential migration of the stiffener wire 38 within the spring cavity. The silicone rubber core 40 also enables the spring of second circumferential segment 36 to prevent axial compression while permitting substantially free radial deformation. As seen in the embodiment illustrated in FIG. 6, the silicone rubber core 40 can be divided into two silicone rubber core segments provided on either side of a spring coupler 41 which joins the ends of the close-coiled spring 30 into a loop. In another embodiment the spring coupler could be provided at one of the second segment, negating the need to divide the core into two segments. The spring coupler 41 holds the ends shown during ventricular systole (i.e., the mitral valve is closed and the left ventricular outflow track is pressurized). The semi-rigid annuloplasty ring 10 is positioned such that right and left trigone markers 18, 20 are coincident to the right and left fibrous trigones 50, 52 of the mitral valve annulus. Anterior leaflet 54 is shown coapting with the posterior leaflet 56 and the anterior portion of the mitral annulus and the leaflet 54 are bowing into the left atrium. The radial seam 26 lies approximately at the midpoint of the posterior portion of the annulus.

Figure 8:
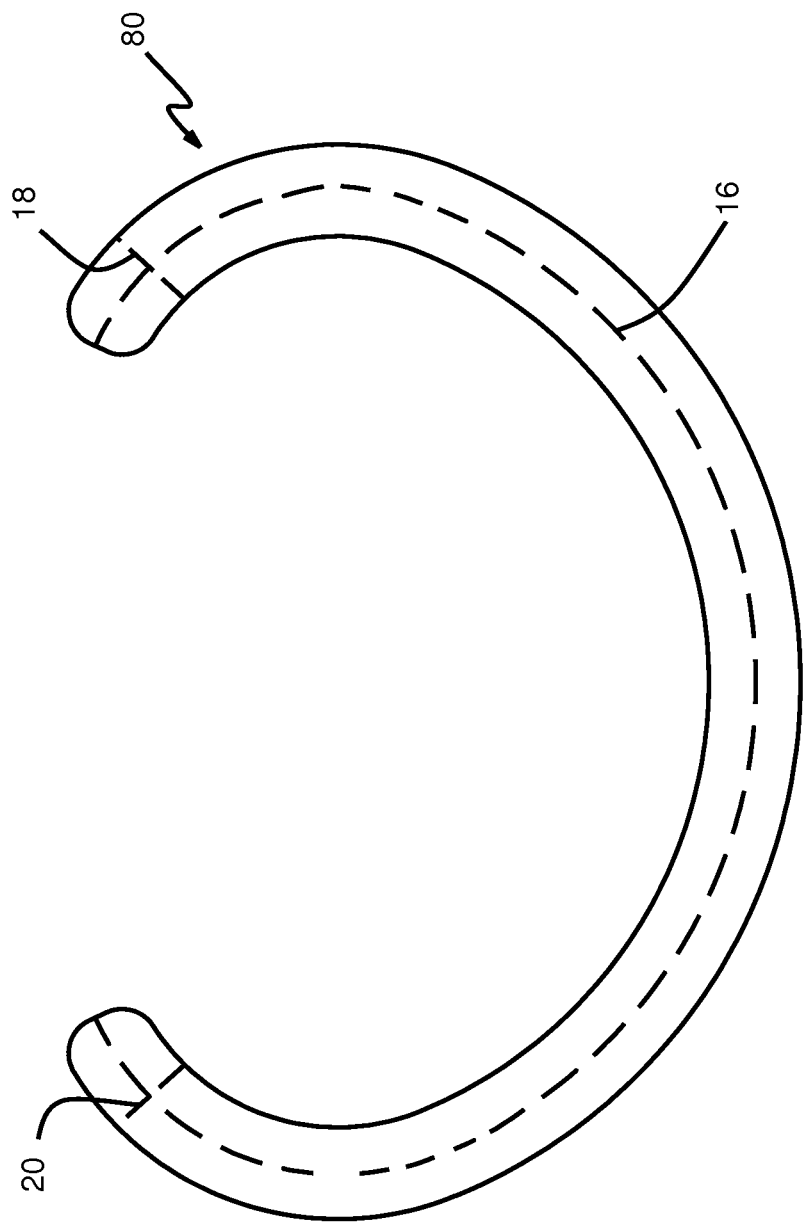
FIG. 8 is a plan view of a semi-rigid annuloplasty band.
Figure 9:
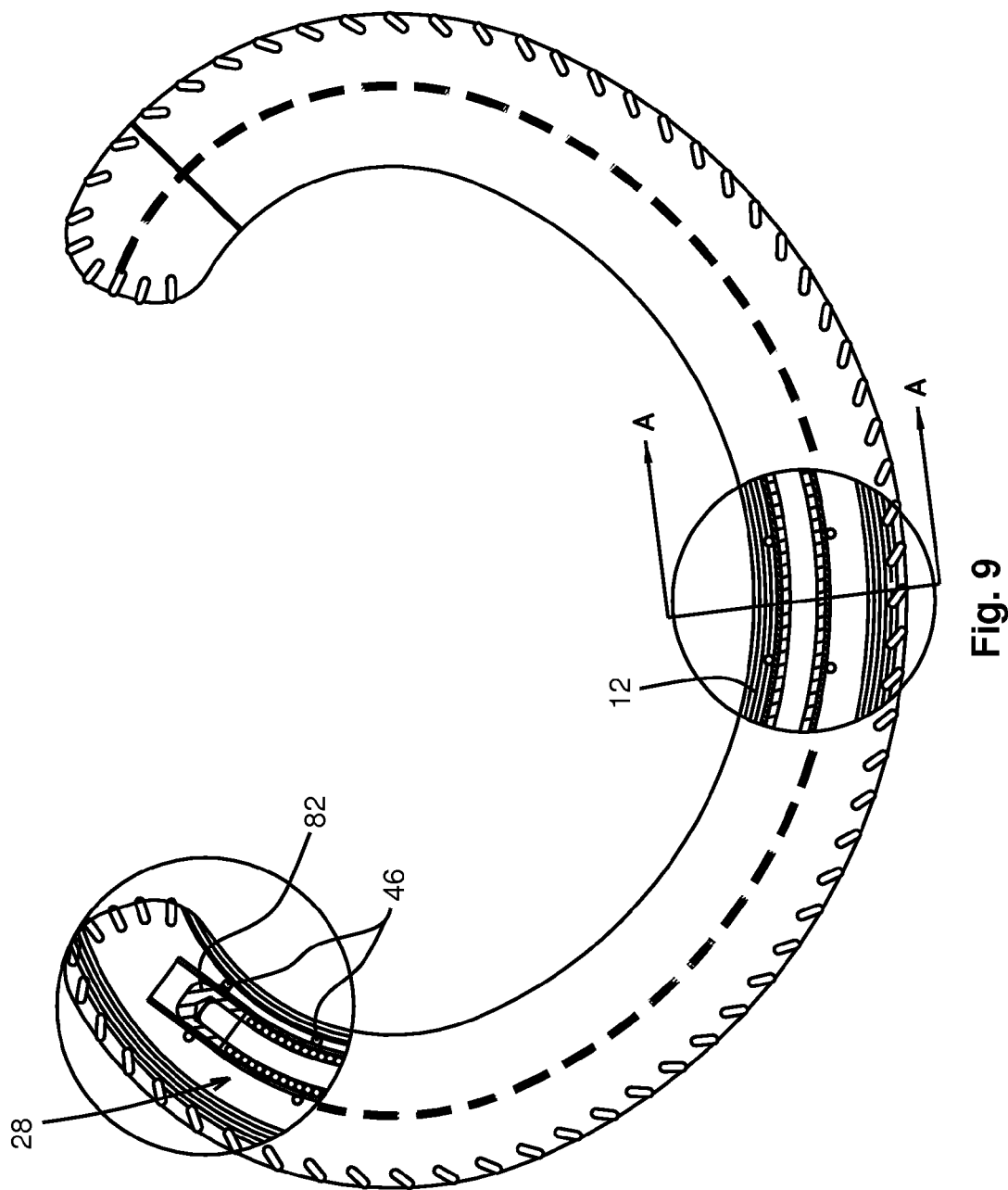
FIG. 9 is a plan view of the semi-rigid annuloplasty band of FIG. 8 with portions cut away to reveal the internal construction.
Figure 10:
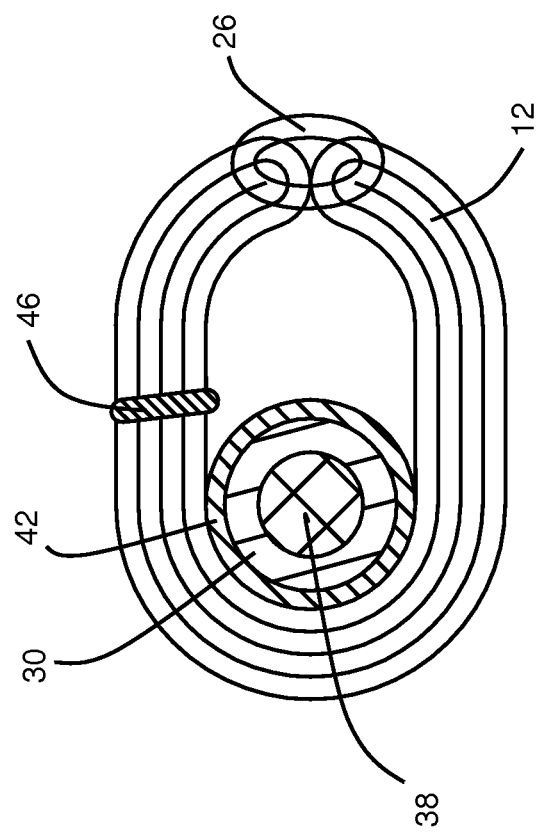
FIG. 10 is a cross-section taken along line A-A of FIG. 9.
Figure 11:
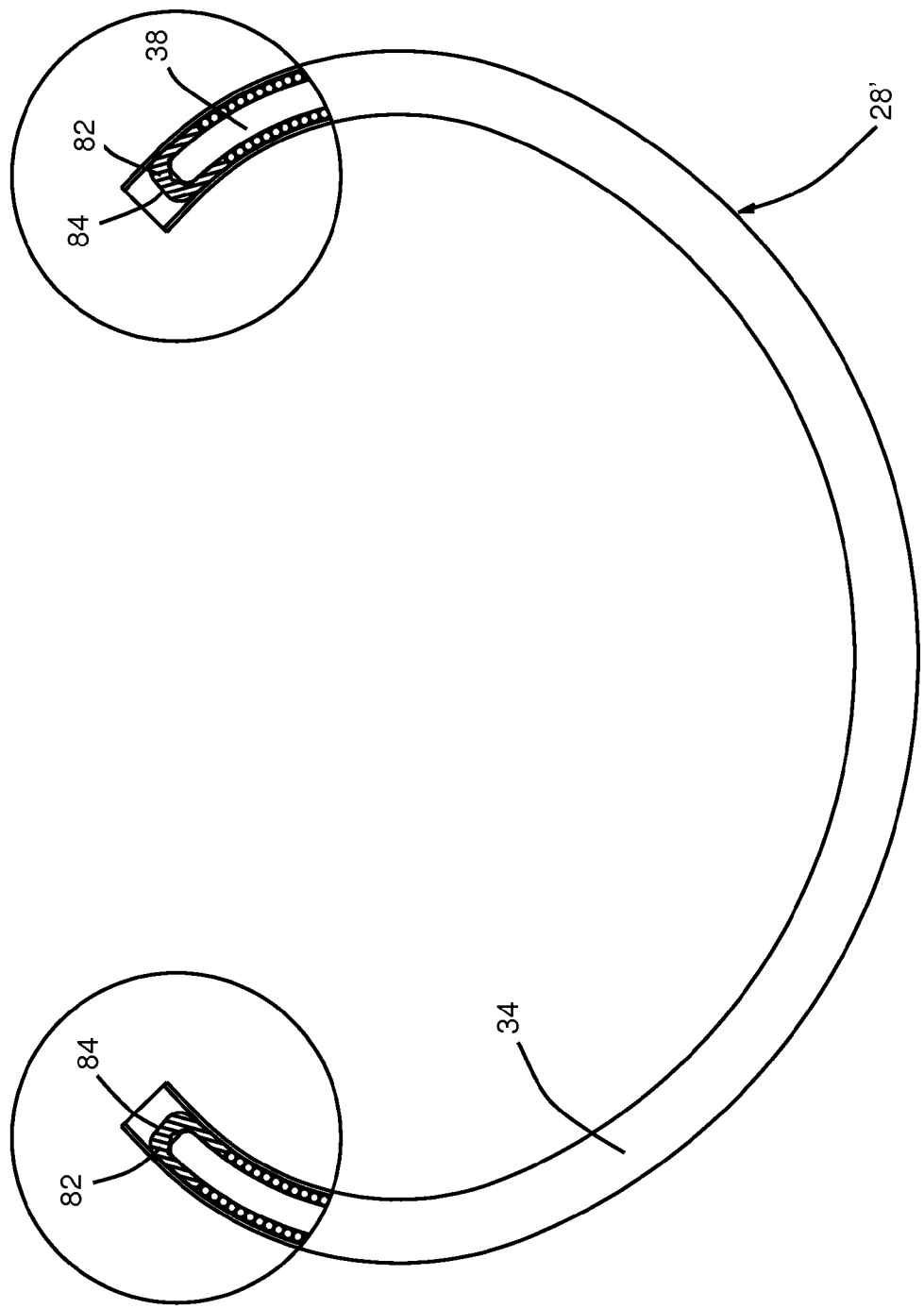
FIG. 11 is a plan view of a semi-rigid stiffener of the annuloplasty ring of FIG. 8 with the suturable cover removed and the ends of the stiffener shown in lengthwise cross-section.

FIGS. 8-12 illustrate a semi-rigid annuloplasty band 80. The semi-rigid annuloplasty band is illustrated as being generally C-shaped. The construction of the semi-rigid annuloplasty band 80 is substantially identical to the posterior portion of the semi-rigid annuloplasty ring 10 described above, including a stiffener assembly substantially identical to the first circumferential segment 34 described above. The same reference numbers are used in FIGS. 8-12 to indicate like elements. The most significant difference between the semi-rigid annuloplasty band 80 and the posterior portion of the semi-rigid annuloplasty ring 10 having the first circumferential segment 34 of the stiffener assembly 28 is the inclusion of end caps 82 on the ends of the stiffener assembly 28'. Referring to FIG. 11, each of the end caps 82 have an inner diameter sized to be press fit over the ends of the stiffener wire 38. In addition, the ends 84 of the end caps are radiused or chamfered remove the sharp edge and may be hemispherical. The end caps are configured to prevent the stiffener from protruding through the suturable material 12 when the semi-rigid annuloplasty band is formed as illustrated in FIGS. 8 and 9. In the illustrated embodiment, the end caps have an outer diameter of about 0.046 inches.

Figure 12:
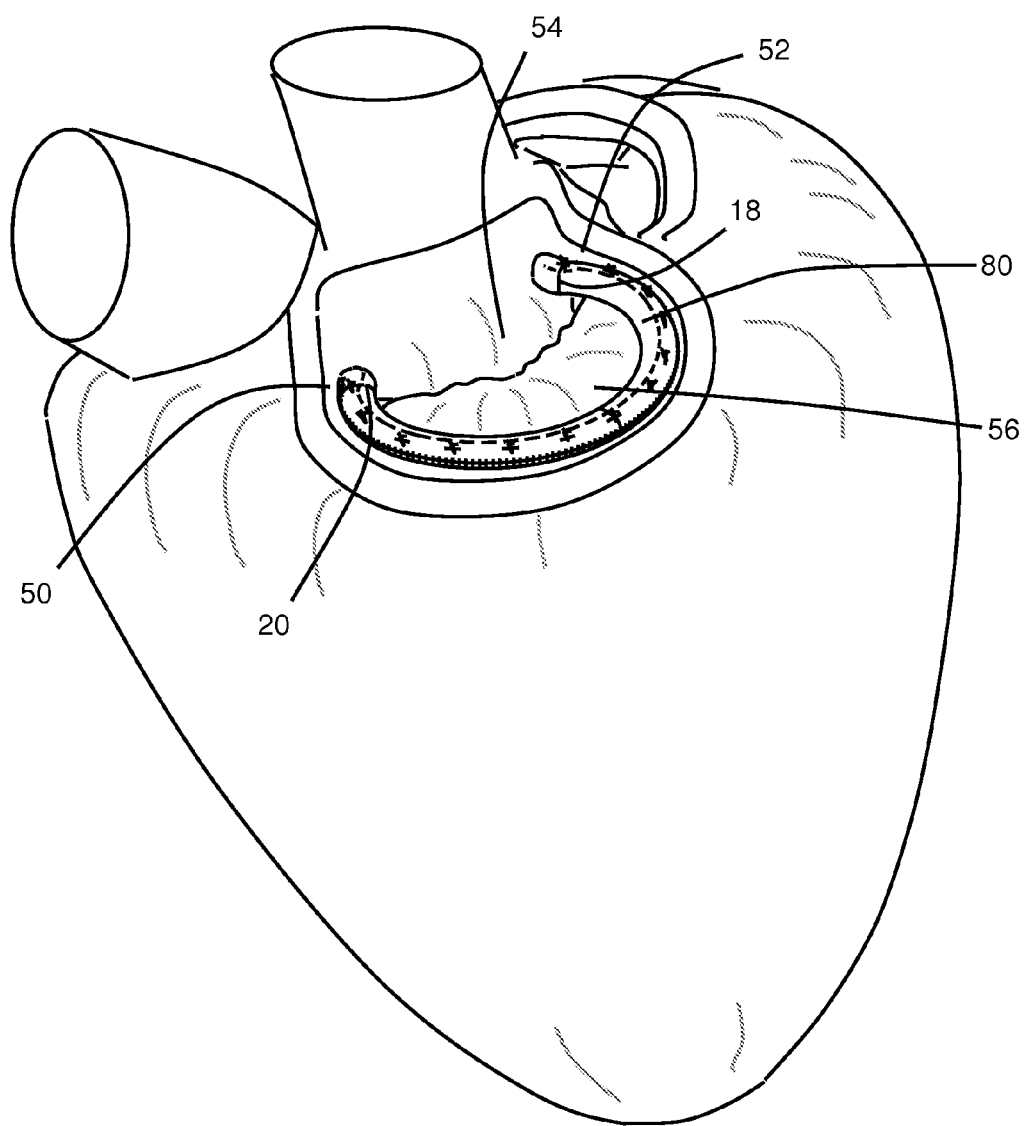
FIG. 12 is an isometric view of a semi-rigid annuloplasty band of FIG. 8 sewn into the mitral annulus of a heart during ventricular systole.

FIG. 12 illustrates the semi-rigid annuloplasty band 80 attached to the mitral annulus of a heart (the left atrium being removed for clarity of illustration). The heart is shown during ventricular systole (i.e., the mitral valve is closed and the left ventricle outflow tract is pressurized). The semi-rigid annuloplasty band 80 is positioned such that the band conforms to the posterior portion of the mitral valve annulus with the ends of the semi-rigid annuloplasty band 80 secured at the left and right trigones. The anterior portion of the mitral valve annulus and the leaflet 54 and thus bow into the left atrium uninhibited.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. An annuloplasty ring comprising:
   an elongate tube of suturable material formed into a ring;
   a close-coiled spring formed into a ring corresponding to the ring of suturable material and received inside the tube, the close-coiled spring including a wire wound to form helical coils of the close-coiled spring;
   a stiffener configured to prevent axial compression and resist radial deformation of the ring received in the tube in a first circumferential segment of the ring of suturable material; and
   an axial support configured to prevent axial compression of the ring and permit substantially free radial deformation of the ring received in the tube in a second circumferential segment of the ring.

2. The annuloplasty ring of claim 1 wherein the stiffener comprises a metal wire axially received in a lengthwise cavity of the close-coiled spring at a circumferential portion of the close-coiled spring corresponding to the first circumferential segment.

3. The annuloplasty ring of claim 2 wherein the axial support comprises a circumferential portion of the close-coiled spring corresponding to the second circumferential segment not having a metal wire axially received therein.

4. The annuloplasty ring of claim 2 further comprising means for maintaining the metal wire in the first circumferential segment.

5. The annuloplasty ring of claim 4 wherein the means for maintaining the metal wire in the first circumferential segment comprises an elastomeric core axially received in the close-coiled spring abutting opposing ends of the metal wire.

6. The annuloplasty ring of claim 5 further comprising a silicone tube axially receiving the close-coiled spring.

7. The annuloplasty ring of claim 6 further comprising the close-coiled spring ring being formed from a single length of close-coiled spring extending between and terminating at opposing, first and second ends, wherein the first and second ends are directly joined to one another by a spring coupler.

8. The annuloplasty ring of claim 2 wherein the metal wire is made of a biocompatible metal having a diameter in a range of 0.15-0.05 inches.

9. The annuloplasty ring of claim 8 wherein the bio-compatible metal is a MP35N alloy.

10. The annuloplasty ring of claim 1 wherein the first circumferential segment of the ring corresponds to a posterior portion of a mitral valve annulus and the first circumferential segment is configured to extend between the annulus trigones.

11. The annuloplasty ring of claim 1 wherein the second circumferential segment corresponds to an anterior portion of a mitral valve annulus and the second circumferential segment is configured to extend between the annulus trigones.

12. The annuloplasty ring of claim 1 wherein the suturable material is a braided heat settable material.

13. The annuloplasty ring of claim 12 wherein the heat settable material is polyethertetraphylate.

14. The annuloplasty ring of claim 1, wherein the close-coiled spring terminates at opposing, first and second ends, the close-coiled spring extending continuously from the first end to the second end, and further wherein a length of the close-coiled spring in extension from the first end to the second end is greater than a length of the stiffener.

* * * * *